US00PP10599P

United States Patent [19]

Verwer

[11] Patent Number: Plant 10,599

[45] Date of Patent: Sep. 8, 1998

[54] DAHLIA PLANT NAMED 'GALLERY PABLO'

[75] Inventor: Aad Verwer, Lisse, Netherlands

[73] Assignee: Gebr. Verwer, Lisse, Netherlands

[21] Appl. No.: 815,863

[22] Filed: Mar. 12, 1997

[51] Int. Cl.[6] ..... A01H 5/00

[52] U.S. Cl. ..... Plt./87.8

[58] Field of Search ..... Plt./87.8

[56] References Cited

U.S. PATENT DOCUMENTS

P.P. 899 11/1949 Gilmore ..... Plt./87.8

OTHER PUBLICATIONS

GTITM UPOVROM List for 'Gallery Pablo' as per PBR DHL 0060 (NL) Mar. 16, 1996.

*Primary Examiner*—James R. Feyrer
*Assistant Examiner*—Kent L. Bell
*Attorney, Agent, or Firm*—C. A. Whealy

[57] ABSTRACT

A distinct cultivar of Dahlia plant named 'Gallery Pablo', characterized by its suitability for potted plants, garden or patio plants, or as cut flowers; upright and spreading, compact and freely branching plant habit; medium green foliage; early and profuse flowering; rapid growth rate; decorative-type inflorescences that are about 10 cm in diameter; yellow and dark pink bi-colored ray florets; and good postproduction longevity.

1 Drawing Sheet

The present invention relates to a new and distinct cultivar of Dahlia plant, botanically known as Dahlia hybrid and referred to by the cultivar name 'Gallery Pablo'.

The new cultivar is a product of a planned breeding program conducted by the inventor in Lisse, The Netherlands. The objective of the breeding program is to create compact Dahlia cultivars that flower early and profusely with desirable ray floret color and good post-production longevity.

The new cultivar originated from a cross made by the inventor in the summer of 1992, of the nonpatented commercial cultivar 'Decorette' as the female, or seed, parent with the nonpatented commercial cultivar 'Extase' as the male, or pollen, parent. Compared to plants of the parent cultivars, the new Dahlia is more compact, more freely branching and inflorescences have a different ray floret color.

The cultivar 'Gallery Pablo' was discovered and selected by the inventor as a flowering plant within the progeny of the stated cross in a controlled environment in Lisse, The Netherlands, in 1992. The selection of this plant was based on its compact and freely branching habit, unique ray floret color, floriferousness and good postproduction longevity.

Asexual reproduction of the new cultivar by terminal cuttings taken in a controlled environment in Lisse, The Netherlands, has shown that the unique features of this new Dahlia are stable and reproduced true to type in successive generations.

The cultivar 'Gallery Pablo' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Gallery Pablo'. These characteristics in combination distinguish 'Gallery Pablo' as a new and distinct cultivar:

1. Suitable for potted plants, garden or patio plants, or as cut flowers.
2. Upright and spreading, compact and freely branching plant habit.
3. Medium green foliage.
4. Early and profuse flowering.
5. Rapid growth rate.
6. Decorative-type inflorescences that are about 10 cm in diameter.

7. Yellow and dark pink bi-colored ray florets.
8. Good postproduction longevity with open inflorescences maintaining good substance and color for about 14 days and plants maintaining good substance and flowering for 3 to 4 months.

The accompanying photograph illustrates the overall appearance of the new cultivar. The colored photograph comprises a side perspective view of a typical flowering plant of 'Gallery Pablo'. This photograph shows the colors as true as it is reasonably possible to obtain in colored reproductions of this type. Floret and foliage colors in the photograph may differ from the actual colors due to light reflectance.

In the following description, color references are made to The Royal Horticultural Society Colour Chart except where general terms of ordinary dictionary significance are used. The following observations and measurements describe plants grown in Lisse, The Netherlands, under conditions which approximate those generally used in commercial potted Dahlia production with day temperatures averaging 21° C. and night temperatures averaging 14° C. Plants were grown during the summer and measurements and numerical values were averages derived from typical flowering plants in September.

Botanical classification: Dahlia hybrid cultivar 'Gallery Pablo'.

Commercial classification: Decorative potted Dahlia.

Parentage:

*Male or pollen parent.*—Dahlia hybrid cultivar 'Extase' (not patented).

*Female or seed parent.*—Dahlia hybrid cultivar 'Decorette' (not patented).

Propagation:

*Type.*—Terminal tip cuttings or by tuberous divisions.

*Time to rooting.*—About 14 days with soil temperatures of 20° C.

*Rooting habit.*—Central root with numerous secondary roots that are fine and fibrous.

Plant description:

*Appearance.*—Perennial herbaceous decorative-type Dahlia, suitable as potted plants, garden or patio plants, or as cut flowers. Upright and spreading, compact habit and freely branching.

*Plant height.*—20 to 25 cm, appropriate for 12 to 15-cm containers.

*Growth rate.*—Rapid, typically only 60 days are required from an unrooted cutting to a finished flowering plant.

*Foliage description.*—Leaf arrangement: Opposite, simple or compound. Compound leaves have either three or five leaflets. Leaf size, single: Length: About 5 cm. Width: About 4 cm. Leaf size, compound: Length: About 15 cm. Width: About 13 cm. Leaf shape: Elliptic. Leaf apex: Acute. Leaf base: Acute. Leaf margin: Serrate. Leaf texture: Smooth. Color: Young foliage adaxial surface: 137C. Young foliage abaxial surface: 191A. Mature foliage adaxial surface: 137A. Mature foliage abaxial surface: 191A. Venation adaxial surface: 146D. Venation abaxial surface: 145C. Petiole: Length: About 4 cm. Color: 145C.

Inflorescence description:

*Appearance.*—Fully double decorative-type inflorescence form with yellow and dark pink bi-colored ray florets. Inflorescences borne on terminals above foliage.

*Flowering response.*—Under natural conditions, plant flower from July to November in the Northern Hemisphere.

*Postproduction longevity.*—On the plant, open inflorescences will maintain good color and substance for at about 14 days. As a cut flower, open inflorescences will maintain good color and substance for at least 6 days. Plants will continue to maintain good substance and flowering for three to four months.

*Quantity of inflorescences.*—Numerous, continuous flowering.

*Inflorescence size.*—Diameter: About 10 cm. Depth (height): About 3 cm.

*Inflorescence bud.*—Size: Length: About 1 cm. Width: About 1.5 cm. Rate of opening: About 14 days. Color: 15 1B.

*Ray florets.*—Shape: Elliptic. Size: Length: About 5 cm. Width: About 2 cm. Apex: Pointed. Margin: Entire. Texture: Smooth, satiny. Aspect: Flat, some undulation. Color: When opening: 47B. Adaxial surface: 1B at base, 47C at center and margins. Abaxial surface: 1A at base, 43D at center.

*Disc florets.*—Few and inconspicuous.

*Peduncle.*—Length: 4 to 20 cm. Aspect: Strong, erect. Texture: Glabrous. Color: 144B with anthocyanin.

*Sepals.*—Quantity: 6 to 7. Shape: Long, narrow, twisted with pointed apex. Color: Abaxial surface: 144A with anthocyanin. Adaxial surface: 144A with anthocyanin.

*Reproductive organs.*—Androecium: Anther shape: Long and pointed. Anther length: About 5 mm Anther color: 17A. Pollen color: 13A. Gynoecium: Stigma color: 17B. Style length: About 3 mm. Style color: 151C with anthocyanin.

Disease resistance: No known Dahlia diseases observed to date on plants grown under commercial conditions.

Seed production: Seed production has not been observed.

It is claimed:

1. A new and distinct cultivar of Dahlia plant named 'Gallery Pablo', as illustrated and described.

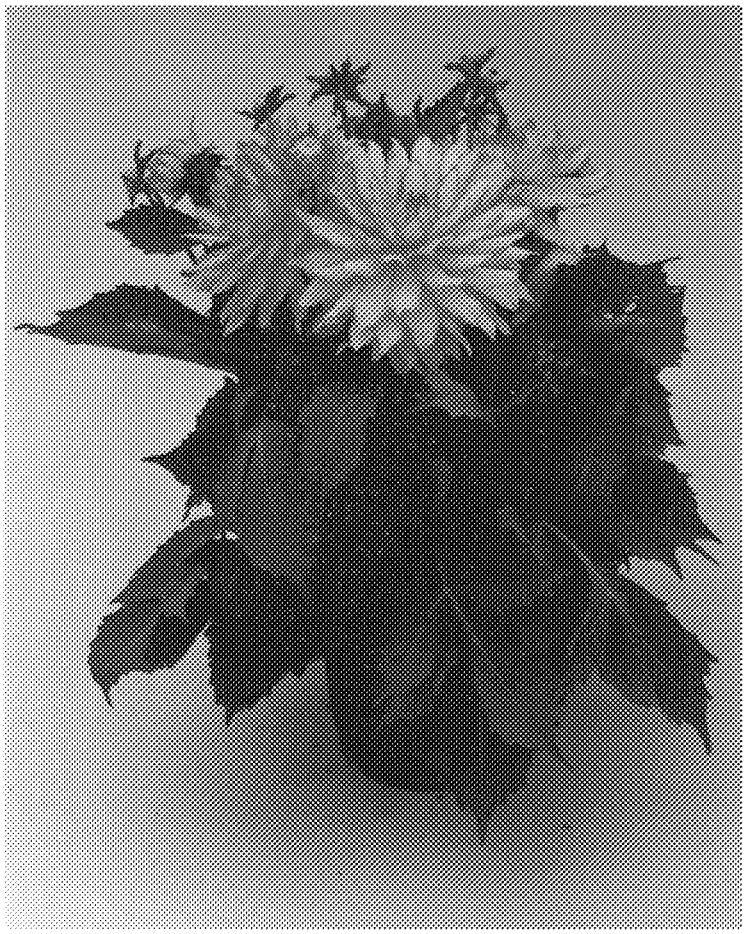

* * * * *